US005712285A

United States Patent [19]
Curtis et al.

[11] Patent Number: 5,712,285
[45] Date of Patent: Jan. 27, 1998

[54] PYRROLO-PYRIDINE DERIVATIVES

[75] Inventors: Neil Roy Curtis, Puckeridge; Janusz Jozef Kulagowski, Bishops Stortford, both of United Kingdom; Paul David Leeson, Monmouth Junction, N.J.; Mark Peter Ridgill, Watton-At-Stone, United Kingdom

[73] Assignee: Merck, Sharp & Dohme, Ltd., Hoddesdon, England

[21] Appl. No.: 626,099

[22] Filed: Apr. 3, 1996

[51] Int. Cl.$^6$ ...................... A61K 31/435; C07D 471/04
[52] U.S. Cl. .................... 514/300; 514/253; 514/256; 514/269; 514/272; 514/274; 544/232; 544/238; 544/310; 544/315; 544/319; 544/324; 544/328; 544/331; 544/333; 544/405; 546/113
[58] Field of Search ........................ 546/113; 514/300

[56] References Cited

U.S. PATENT DOCUMENTS

| | | |
|---|---|---|
| 3,362,956 | 1/1968 | Archer . |
| 3,511,841 | 5/1970 | Archer . |
| 3,969,527 | 7/1976 | Krapcho et al. . |
| 4,291,042 | 9/1981 | Ward . |
| 5,212,195 | 5/1993 | Clark et al. . |
| 5,432,177 | 7/1995 | Bailer et al. . |
| 5,563,150 | 10/1996 | Curtis et al. . |
| 5,563,152 | 10/1996 | Kulagowski et al. . |

FOREIGN PATENT DOCUMENTS

WO 94/20497  9/1994  WIPO .

OTHER PUBLICATIONS

Lorenz, R. R. et al. "A New Indole Synthesis", vol. 30, Aug. 1995, pp. 2531–2533 *J. Org. Chem.* .

Estel, L. et al. J. Org. Chem. 1988, (53), pp. 2740–2744 "Metalation/S$_{RN}$1 Coupling in Heterocyclic Synthesis".

Sakamoto, T. et al. Heterocycles, vol. 34, No. 12, 1992 pp. 2379–2384 "Condensed Heteroaromatic Ring Systems".

Clark, R. D. et al. Synthesis Oct. 1991, pp. 871–878 "Preparation of Indoles and Oxidoles from N–(e–Butoxy carbonyl)–2–alkylanilines".

Archer, S. 25523t, Chem Abstracts vol. 73, 1970 p.375 "1–[4–;5–. 6– and 7–Azaindolyl) lower alkyl]–4–substituted piperazines".

Archer, S. 10467w, Chem Abstracts vol. 69, 1968, p.1000 "1–[(Heterocyclyl)–lower–alkyl]–4–Substituted–piperazines".

*Primary Examiner*—Patricia L. Morris
*Attorney, Agent, or Firm*—Robert J. North; Melvin Winokur

[57] ABSTRACT

A class of pyrrolo[2,3-b]pyridine derivatives, linked via the 3-position thereof by a methylene group to a tetrahydropyridinyl moiety, the latter moiety being substituted in turn by an aryl- or heteroaryl-substituted divalent monocyclic radical, are ligands for dopamine receptorsubtypes within the body, in particular the $D_4$ subtype, and are accordingly of use in the treatment and/or prevention of disorders of the dopamine system, including schizophrenia and depression.

7 Claims, No Drawings

PYRROLO-PYRIDINE DERIVATIVES

This invention relates to a particular class of heteroaromatic compounds. More particularly, the invention is concerned with certain substituted tetrahydropyridinylmethyl derivatives of pyrrolo[2,3-b]-pyridine. These compounds are ligands for dopamine receptor subtypes within the body, in particular the dopamine $D_4$ receptor subtype. They are therefore of use in the treatment and/or prevention of disorders of the dopamine system, including schizophrenia, depression, anxiety, nausea, Parkinson's disease, tardive dyskinesias and extrapyramidal side-effects associated with treatment by conventional neuroleptic agents, neuroleptic malignant syndrome, disorders of hypothalamic-pituitary function such as hyperprolactinaemia and amenorrhoea, and delusional disorders (cf. Catalano et al., *Biol. Psychiatry*, 1993, 34, 459).

Upper gastrointestinal tract motility is believed to be under the control of the dopamine system. The compounds according to the present invention may thus be of use in the prevention and/or treatment of gastrointestinal disorders, and the facilitation of gastric emptying.

Dependence-inducing agents such as cocaine and amphetamine have been shown to interact with the dopamine system. Compounds capable of counteracting this effect, including the compounds in accordance with the present invention, may accordingly be of value in the prevention or reduction of dependence on a dependence-inducing agent.

Dopamine is known to be a peripheral vasodilator; for example, it has been shown to exert a dilatory effect on the renal vascular bed. This implies that the compounds of the present invention may be beneficial in controlling vascular blood flow.

The localisation of dopamine receptor mRNA in rat heart and large vessels has been noted. This suggests a role for dopamine receptor ligands in controlling cardiovascular function, either by affecting cardiac and smooth muscle contractility or by modulating the secretion of vasoactive substances. The compounds according to the present invention may therefore be of assistance in the prevention and/or treatment of such conditions as hypertension and congestive heart failure.

By virtue of their activity as ligands for dopamine receptor subtypes within the body, the compounds in accordance with the present invention may also be of benefit in enhancing cognitive function, and in treating and/or preventing cognitive disorders including presenile and senile dementia (also known as Alzheimer's disease and senile dementia of the Alzheimer type respectively).

Molecular biological techniques have revealed the existence of several subtypes of the dopamine receptor. The dopamine $D_1$ receptor subtype has been shown to occur in at least two discrete forms. Two forms of the $D_2$ receptor subtype, and at least one form of the $D_3$ receptor subtype, have also been discovered. More recently, the $D_4$ (Van Tol et al., *Nature* (London), 1991, 350, 610) and $D_5$ (Sunahara et al., *Nature* (London), 1991, 350, 614) receptor subtypes have been described.

WO-A-94/20459 describes a class of pyrrolo[2,3-b] pyridine derivatives, linked via the 3-position thereof by a methylene group to inter alia a substituted tetrahydropyridinyl moiety. These compounds are stated therein to be ligands for dopamine receptor subtypes within the body, and therefore to be useful for the treatment and/or prevention of disorders of the dopamine system, in particular schizophrenia. It has now been found that a related series of pyrrolo[2,3-b]pyridine derivatives, substituted on the tetrahydropyridinyl moiety by an aryl- or heteroaryl-substituted divalent monocyclic radical, are ligands for dopamine receptor subtypes within the body, in particular the $D_4$ receptor subtype, possessing advantageous properties in terms of enhanced metabolic stability, and are accordingly of use in the treatment and/or prevention of disorders of the dopamine system, including schizophrenia and depression.

The present invention provides a compound of formula I, or a salt or prodrug thereof:

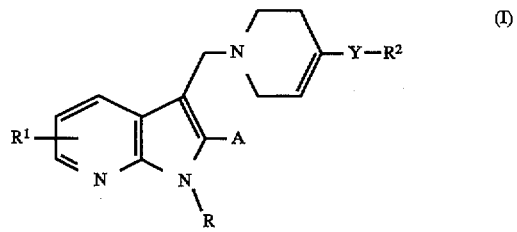

wherein

A represents hydrogen, $C_{1-6}$ alkyl, $C_{1-6}$ alkoxy, halogen, cyano or trifluoromethyl;

$R^1$ represents hydrogen, halogen, cyano, nitro, trifluoromethyl, amino, $C_{1-6}$ alkylamino, di($C_{1-6}$) alkylamino, $C_{1-6}$ alkyl, $C_{1-6}$ alkoxy, aryl($C_{1-6}$)alkoxy or $C_{2-6}$ alkylcarbonyl;

Y represents a divalent monocyclic radical selected from the following groups of formula Ya to Yg:

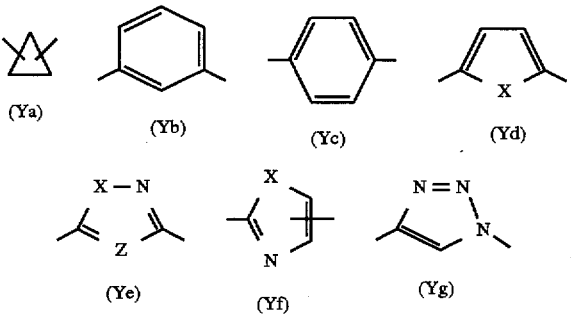

in which X represents oxygen, sulphur or N—$R^3$;

Z represents CH or N;

R and $R^3$ independently represent hydrogen or $C_{1-6}$ alkyl; and $R^2$ represents an optionally substituted aryl or heteroaryl group.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Where R² represents an optionally substituted aryl group, this is suitably an optionally substituted phenyl or naphthyl group.

Where R² represents an optionally substituted heteroaryl group, examples of suitable groups typically include optionally substituted pyridyl, quinolyl, isoquinolyl, pyridazinyl, pyrimidinyl, pyrazinyl, pyranyl, furyl, benzofuryl, dibenzofuryl, thienyl, benzthienyl, pyrrolyl, indolyl, pyrazolyl, indazolyl, imidazolyl, benzimidazolyl, oxazolyl, isoxazolyl, oxadiazolyl, thiazolyl, isothiazolyl and thiadiazolyl groups.

The aryl or heteroaryl group R² may be optionally substituted by one or more groups selected from $C_{1-6}$ alkyl, adamantyl, phenyl, aryl($C_{1-6}$)alkyl, halogen, $C_{1-6}$ haloalkyl, $C_{1-6}$ aminoalkyl, trifluoromethyl, hydroxy, $C_{1-6}$ alkoxy, aryloxy, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, trifluoromethanesulphonyloxy, —NR$^v$R$^w$, —NR$^v$COR$^w$, —NR$^v$CO$_2$R$^w$, —NR$^v$SO$_2$R$^w$, —CH$_2$NR$^v$SO$_2$R$^w$, —NHCONR$^v$R$^w$, —PO(OR$^v$)(OR$^w$), —CONR$^v$R$^w$, —SO$_2$NR$^v$R$^w$ and —CH$_2$SO$_2$NR$^v$R$^w$, in which R$^v$ and R$^w$ independently represent hydrogen, $C_{1-6}$ akyl, aryl or aryl($C_{1-6}$)akyl.

As used herein, the expression "$C_{1-6}$ akyl" relates to methyl and ethyl groups, and straight-chained or branched propyl, butyl, pentyl and hexyl groups. Particular alkyl groups include methyl, ethyl, n-propyl, isopropyl and t-butyl. Derived expressions such as "$C_{1-6}$ alkoxy", "$C_{1-6}$ akylamino" and di($C_{1-6}$) are to be construed accordingly.

The term "halogen" as used herein includes fluorine, chlorine, bromine and iodine, especially fluorine or chlorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In particular, where Y represents a moiety of formula Ya, the substituents on the cyclopropyl ring may give rise to cis and trans diastereoisomers, with the trans orientation being preferred.

Suitably, the substituent A represents hydrogen or $C_{1-6}$ alkyl, in particular hydrogen or methyl, and especially hydrogen.

Suitably, the substituent R represents hydrogen or methyl, especially hydrogen.

Particular values for the substituent R¹ include hydrogen, fluoro, chloro, methyl, methoxy and benzyloxy, especially hydrogen.

Examples of optional substituents on the group R² include $C_{1-6}$ alkyl, halogen, cyano, nitro, trifluoromethyl, $C_{1-6}$ alkoxy, di($C_{1-6}$)alkylamino, aryloxy and arylcarbonyloxy, in particular methyl, fluoro, chloro, cyano, nitro, trifluoromethyl, methoxy, dimethylamino, phenoxy and benzoyloxy, and especially chloro.

Particular values of R² include phenyl, fluorophenyl, chlorophenyl, methylphenyl, methoxyphenyl and pyridyl, especially phenyl,chlorophenyl and pyridyl.

Suitably, R³ represents hydrogen or methyl, especially methyl.

In the structures of formula Yd, Ye and Yf, the moiety X is suitably oxygen or sulphur.

In the structure of formula Yf, the substituent R² is suitably attached to the carbon atom adjacent to the moiety X.

One sub-class of compounds according to the invention is represented by the compounds of formula IIA, and salts and prodrugs thereof:

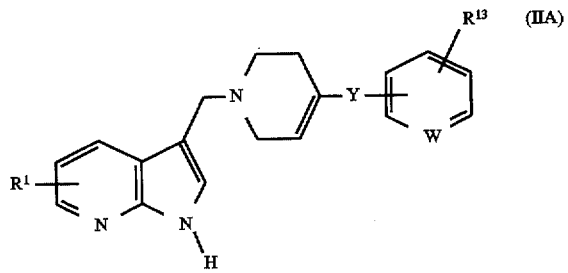

wherein

R¹ and Y are as defined with reference to formula I above;

W represents CH or N; and

R¹³ represents hydrogen, halogen, cyano, nitro, trifluoromethyl, $C_{1-6}$ alkyl, $C_{1-6}$ alkoxy or di($C_{1-6}$) alkylamino.

In relation to formula IIA above, R¹ is suitably hydrogen.

Particular values of R¹³ include hydrogen, fluoro, chloro, cyano, nitro, trifluoromethyl, methyl, methoxy and dimethylamino, especially hydrogen or chloro.

Specific compounds within the scope of the present invention include:

3-[4-(3-phenylisoxazol-5-yl)-1,2,3,6-tetrahydropyridin-1-yl]methylpyrrolo[2,3-b]pyridine;

3-[4-(3-(pyridine-3-yl)isoxazol-5-yl)-1,2,3,6-tetrahydropyridin-1-yl]methylpyrrolo[2,3-b]pyridine;

3-[4-(3-(4-chlorophenyl)isoxazol-5-yl)-1,2,3,6-tetrahydropyridin-1-yl]methylpyrrolo[2,3-b]pyridine;

3-[4-(1-phenyl-1,2,3-triazol-4-yl)-1,2,3,6-tetrahydropyridin-1-yl]methylpyrrolo[2,3-b]pyridine;

3-[4-(3-biphenyl)-1,2,3,6-tetrahydropyridin-1-yl]methylpyrrolo[2,3-b]pyridine;

3-[4-(4-biphenyl)-1,2,3,6-tetrahydropyridin-1-yl]methylpyrrolo[2,3-b]pyridine;

3-[4-(3-phenyl-1,2,4-oxadiazol-5-yl)-1,2,3,6-tetrahydropyridin- 1-yl]methylpyrrolo[2,3 -b]pyridine;

3-[4-(5-phenyloxazol-2-yl)-1,2,3,6-tetrahydropyridin-1-yl]methylpyrrolo[2,3-b]pyridine;

3-[4-(5-phenylthien-2-yl)-1,2,3,6-tetrahydropyridin-1-yl]methylpyrrolo[2,3-b]pyridine;

trans-3-[4-(2-phenylcyclopropyl-1-yl)-1,2,3,6-tetrahydropyridin-1-yl]methylpyrrolo[2,3-b]pyridine;

and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Favoured unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of schizophrenia or depression, a suitable dosage level is about 0.001 to 250 mg/kg per day, preferably about 0.005 to 100 mg/kg per day, and especially about 0.01 to 5 mg/kg per day. The compounds may be administered on a regimen of 1 to 4 times per day.

In order to alleviate the symptoms of schizophrenia without causing sedation or extrapyramidal side-effects, it is believed that the dosage level of the active ingredient should be selected such that the dose administered is effective in substantially completely blocking the dopamine $D_4$ receptor subtype in human brain whilst displaying no or negligible $D_2$ receptor subtype occupancy. A suitable dosage level in this regard is about 0.001 to 5.0 mg/kg per day, more particularly about 0.005 to 1.0 mg/kg per day, and especially about 0.01 to 0.5 mg/kg per day.

If desired, the compounds in accordance with this invention may be co-administered with another medicament, for example a known anti-schizophrenic agent which produces its effects via dopamine $D_2$ and/or $5-HT_2$ receptor blockade.

Such co-administration may be desirable where a patient is already on an established treatment regime, for example one involving conventional anti-schizophrenic medicaments such as haloperidol or chlorpromazine.

The compounds in accordance with the present invention may be prepared by a process which comprises reacting a compound of formula III with a compound of formula IV:

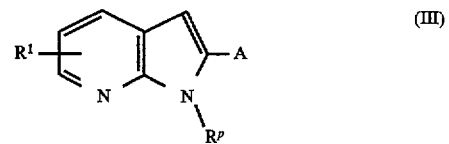

(III)

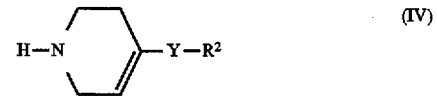

(IV)

wherein A, $R^1$, Y and $R^2$ are as defined above, and $R^P$ corresponds to the group R as defined above or represents a suitable protecting group; in the presence of a substantially equimolar amount of formaldehyde; followed, where required, by removal of the protecting group $R^P$; and subsequently, if necessary, N-alkylation by standard methods to introduce the moiety R.

The reaction is conveniently carried out by stirring the reactants in a solvent such as isopropanol or aqueous acetic acid, optionally in the presence of a buffer such as sodium acetate trihydrate.

The formaldehyde may be utilised in the form of paraformaldehyde; or as a solution of formaldehyde in an inert solvent, e.g. 37% aqueous formaldehyde.

The protecting group $R^P$, when present, is suitably an acyl moiety such as acetyl, which can conveniently be removed as necessary by treatment under strongly basic conditions, e.g. sodium methoxide in methanol. Alternatively, the protecting group $R^P$ may be a carbamoyl moiety such as t-butoxycarbonyl (BOC), which can conveniently be removed as necessary by treatment under mildly acidic conditions.

In an alternative procedure, the compounds according to the present invention may be prepared by a process which comprises reacting a compound of formula IV as defined above with a compound of formula V:

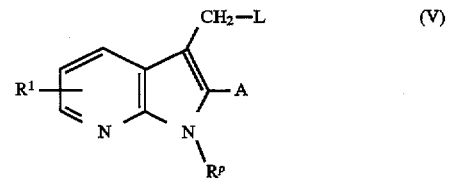

(V)

wherein A, $R^1$ and $R^P$ are as defined above, and L represents a suitable leaving group; followed, where required, by removal of the protecting group $R^P$; and subsequently, if necessary, N-alkylation by standard methods to introduce the moiety R.

The leaving group L is suitably a halogen atom, e.g. chlorine or bromine; or a dialkylamino group, e.g. dimethylamino.

When L represents a halogen atom, the reaction between compounds IV and V is conveniently carried out by stirring the reactants under basic conditions in a suitable solvent, for example potassium carbonate in N,N-dimethylformamide, or triethylamine in tetrahydrofuran or acetonitrile. Where L represents a dialkylamino group, the reaction is conveniently effected by heating the reactants in an inert solvent such as toluene, typically at the reflux temperature of the solvent.

Where they are not commercially available, the starting materials of formula III, IV and V may be prepared by procedures analogous to those described in the accompanying Examples, or by standard methods well known from the art.

It will be appreciated that any compound of formula I initially obtained from any of the above processes may, where appropriate, subsequently be elaborated into a further desired compound of formula I using techniques known from the art. For example, a compound of formula I wherein R is hydrogen initially obtained may be converted into a compound of formula I wherein R represents $C_{1-6}$ alkyl by standard alkylation techniques, such as by treatment with an alkyl iodide, e.g. methyl iodide, typically under basic conditions, e.g. sodium hydride in dimethylformamide, or triethylamine in acetonitrile.

Where the above-described processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds useful in this invention potently inhibit [$^3$H]-spiperone binding to human dopamine $D_4$ receptor subtypes expressed in clonal cell lines.

[$^3$H]-Spiperone Binding Studies

Clonal cell lines expressing the human dopamine $D_4$ receptor Subtype were harvested in PBS and then lysed in 10 mM Tris-HCl pH 7.4 buffer containing 5 mM $MgSO_4$ for 20 min on ice. Membranes were centrifuged at 50,000 g for 15 min at 4° C. and the resulting pellets resuspended in assay buffer (50 mM Tris-HCl pH 7.4 containing 5 mM EDTA, 1.5 mM $CaCl_2$, 5 mM $MgCl_2$, 5 mM KCl, 120 mM NaCl, and 0.1% ascorbic acid) at 20 mg/ml wet weight. Incubations were carried out for 60 min at room temperature (22° C.) in the presence of 0.05–2 nM [$^3$H]-spiperone or 0.2 nM for displacement studies and were initiated by addition of 20–100 μg protein in a final assay volume of 0.5 ml. The incubation was terminated by rapid filtration over GF/B filters presoaked in 0.3% PEI and washed with 10 ml ice-cold 50 mM Tris-HCl, pH 7.4. Specific binding was determined by 10 μM apomorphine and radioactivity determined by counting in a LKB beta counter. Binding parameters were determined by non-linear least squares regression analysis, from which the inhibition constant $K_i$ could be calculated for each test compound.

The compounds of the accompanying Examples were tested in the above assay, and all were found to possess a $K_i$ value for displacement of [$^3$H]-spiperone from the human dopamine $D_4$ receptor subtype of below 1.5 μM.

EXAMPLE 1

3-[4-(3-Phenylisoxazol-5-yl)-1,2,3,6-tetrahydropyridin-1-yl]methylpyrrolo[2,3-b]pyridine Step 1: 1-tert-Butoxycarbonyl-4-piperidone Triethylamine (92 ml, 0.66 mol) was added dropwise to a cold (0° C.) suspension of 4-piperidone monohydrate hydrochloride (100 g, 0.65mol) and di-tert-butyl dicarbonate (142 g, 0.65 mol) in dichloromethane (400 ml) under a nitrogen atmosphere. The cooling bath was removed when about a quarter of the triethylamine had been added.

After 2 hours stirring at room temperature the vigorous bubbling had ceased, the mixture was diluted with water (500 ml), the phases were separated and the aqueous was extracted with dichloromethane (3×250 ml). The combined organic layers were washed with brine (250 ml), dried ($MgSO_4$) and evaporated in vacuo to give a light brown solid. The solid was dissolved in ethyl acetate (1 l) and treated with silica gel (150 g). Filtration and evaporation gave the title compound as a white waxy solid (111.7 g, 86%);δH($CDCl_3$) 1.49 (9H, s, OC($CH_3$)$_3$),2.44 (4H, t, J 6.1 Hz, 2×piperidone $CH_2CO$) and 3.72 (4H, t, J 6.1 Hz, 2×piperidone $CH_2$-N).

Step 2: 1-tert-Butoxycarbonyl-4-trimethylsilylethynyl-1,2,3,6-tetrahydropyridine n-Butyl lithium (2.5M in hexanes, 110 ml, 276 mmol) was cannulated into a solution of trimethylsilylacetylene (40 ml, 276 mmol) in tetrahydrofuran (500 ml) at −70° C., under a nitrogen atmosphere, at such a rate that the temperature did not exceed −60° C. Once the addition was complete the solution was stirred at −70° C. for one hour. The cooling bath was removed and the solution was cannulated into a solution of 1-tert-butyloxycarbonyl-4-piperidone in THF (500 ml) at −70° C. under a nitrogen atmosphere at such a rate that the temperature did not exceed −65° C. Once the addition was complete the mixture was stirred at −70° C. for 10 minutes before warming to room temperature. After stirring for one hour at room temperature the mixture was cooled to 0° C. and saturated ammonium chloride (500 ml) was added. The solvent was removed in vacuo and the residue extracted with dichloromethane (3×500 ml). The organic layers were dried ($MgSO_4$) and evaporated in vacuo to give an orange residue (89 g). The residue was dissolved in dichloromethane (1 l) under a nitrogen atmosphere, triethylamine (52.5 ml, 375 mmol) was added and the mixture was cooled to −10° C. Mesyl chloride (22 ml, 278 mmol) was then added at such a rate that the temperature did not exeed 0° C. Once the addition was complete the mixture was stirred at 0° C. for 10 minutes, allowed to warm to room temperature and stirred for 20 hours.

The solution was treated with sodium bicarbonate (sat., 400 ml), the phases were separated and the aqueous layer extracted with dichloromethane (2×250 ml). The combined organic layers were washed with brine (250 ml), dried ($MgSO_4$) and evaporated in vacuo to give a pale oil which was purified by column chromatography on silica gel, eluting with ethyl acetate/petroleum ether 60/80 (1:1), to give the title compound (51 g, 72%) as a pale straw coloured oil; δH ($CDCl_3$) 1.46 (9H, s, OC($CH_3$)$_3$), 2.24 (2H, br s, tetrahydropyridinyl $CH_2$), 3.47 (2H, t, J 5.6 Hz, tetrahydropyridinyl $CH_2$), 4.12 (2H, d, J 7.1 Hz, tetrahydropyridinyl $CH_2$) and 6.06 (1H, br s, tetrahydropyridinyl CH).

Step 3: 1-tert-Butoxycarbonyl-4-ethynyl-1,2,3,6-tetrahydropyridine

Potassium carbonate (1.0 g, 7.2 mmol) was added to a solution of 1-tert-butoxycarbonyl-4-trimethylsilylethynyl-1,2,3,6-tetrahydropyridine (44.9 g, 16 lmmol) in methanol (250 ml) under a nitrogen atmosphere and the mixture was stirred at room temperature for 3 hours. The solution was evaporated in vacuo without heating. The residue was dissolved in ether (250 ml), washed with sodium carbonate (sat., 100 ml), water (50 ml) and brine (50 ml) before drying (MgSO$_4$) and evaporation in vacuo to give the title compound as a white waxy solid (30.0 g, 90%); δH (CDCl$_3$) 1.46 (9H, s, OC(CH$_3$)$_3$), 2.24–2.26 (2H, m, tetrahydropyridinyl CH$_2$), 2.89 (1H, s, ethynyl CH), 3.49 (2H, t, J 5.7 Hz, tetrahydropyridinyl CH$_2$), 3.95–3.97 (2H, m, tetrahydropyridinyl CH$_2$) and 6.10 (1H, s, tetrahydropyridinyl CH).

Step 4: 1-tert-Butoxycarbonyl-4-(3-phenylisoxazol-5-yl)-1,2,3,6-tetrahydropyridine To a solution of syn-benzaldehyde oxime (1.16 g, 9.7 mmol) in DMF (40 ml) at 0° C. under nitrogen was added a solution of N-bromosuccinmide (2.57 g, 14.4 mmol) in DMF, keeping the temperature below 0° C. When addition was complete the resultant yellow solution was stirred initally at 0° C. and then at room temperature for 1 hour. The reaction was then cooled to 0° C. and triethylamine (2 ml, 14.4 mmol) and the foregoing acetylene (2 g, 9.7 mmol) added. The reaction was stirred at room temperature for 18 hours, diluted with H$_2$O (400 ml) and extracted with ethyl acetate (3×100 ml). The combined organic layers were washed with H$_2$O (50 ml), saturated brine (50 ml), dried (MgSO$_4$) and evaporated in vacuo to yield an oil. Purification by column chromatography on silica eluting with 25% ethyl acetate/petroleum ether (60°–80°) gave the title compound as an off-white solid (1.58 g, 50%) δH (CDCl$_3$) 1.49 (9H, s, OC(CH$_3$)$_3$), 2.50–2.55 (2H, m, tetrahydropyridinyl CH$_2$), 3.65 (2H, t, J 8.2, tetrahydropyridinyl CH$_2$), 4.13–4.17 (2H, m, tetrahydropyridinyl CH$_2$), 6.45 (1H, s, isoxazolyl 4-H), 6.56 (1H, br s, tetrahydropyridinyl 5-H), 7.39–7.51 (3H, m, ArH), 7.77–7.83 (2H, m, ArH).

Step 5: 4-(3-Phenylisoxazol-5-yl-1,2,3,6-tetrahydropyridine

To a solution of the foregoing tetrahydropyridine (1.75 g, 5.4 mmol) in dichloromethane (10 ml) was added trifluoroacetic acid (10 ml) and the reaction stirred at room temperature for 15 minutes. The solvent was evaporated in vacuo, the residue basified with aqueous sodium hydroxide solution (1M, 30 ml), and extracted with dichloromethane (3×30 ml). The combined organic extracts were washed with saturated brine (10 ml), dried (K$_2$CO$_3$) and evaporated in vacuo to give the title compound as a yellow solid (1.1 g, 90%). δH (CDCl$_3$) 1.72 (1H, br s, NH), 2.42–2.46 (2H, m, tetrahydropyridinyl CH$_2$), 3.11 (2H, t, J 5.7Hz, tetrahydropyridinyl CH$_2$), 3.57–3.60 (2H, m, tetrahydropyridinyl CH$_2$), 6.41 (1H, s, isoxazolyl 4-H), 6.39 (1H, br s, tetrahydropyridinyl 5-H), 7.42–7.48 (3H, m, ArH), 7.78–7.82 (2H, m, ArH).

Step 6: 3-[4-(3-Phenylisoxazol-5-yl)-1,2,3,6-tetrahydropyridin-1-yl]methylpyrrolo [2,3-b]pyridine A mixture of the foregoing tetrahydropyridine (750mg, 3.3 mmol) and 3-dimethylaminomethyl-1H-pyrrolo[2,3-b]pyridine (609 mg, 3.5 mmol) in toluene (30 ml) was stirred at reflux for 8 hours under a nitrogen atmosphere, during which time a solid separated. The reaction was coded to room temperature and the precipitate collected by filtration to yield the title compound (350 mg, 30%), mp 224°–226° C. (toluene); (found: C, 73.80; H, 5.54; N, 15.31; C$_{22}$H$_{20}$N$_4$O requires C, 73.76; H, 5.68; N, 15.64%); δH (DMSO-d$_6$) 2.47 (2H, br s, tetrahydropyridinyl CH$_2$), 2.68 (2H, t, J 6.0Hz, tetrahydropyridinyl CH$_2$), 3.17 (2H, br s, tetrahydropyridinyl CH$_2$), 3.78 (2H, s, ArCH$_2$N), 6.55 (1H, br s, tetrahydropyridinyl 5-H), 7.02–7.05 (2H, m, 5-H, isoxazolyl 5-H), 7.41 (1H, d, J 2.3Hz, 2-H), 7.49–7.52 (3H, m, ArH), 7.84–7.87 (2H, m, ArH), 8.05 (1H, d, J 7.8 Hz, 4-H), 8.20 (1H, dd, J 4.8, 1.5Hz, 6-H), 11.49 (1H, br s, NH); m/z (ES$^+$) 357 (M+1)$^+$.

EXAMPLE 2

3-[4-(3-(Pyridin-3-yl)isoxazol-5-yl)-1,2,3,6-tetrahydropyrin-1-yl]methylpyrrolo[2,3-b]pyridine M.p. 233°–235° C. (dec.) (propan-2-ol); (found: C, 70.39; H, 5.38; N, 19.14; C$_{21}$H$_{19}$N$_5$O, 0.07 (C$_3$H$_8$O) requires C, 70.45; H, 5.45; N, 19.37%); δH (DMSO-d$_6$) 2.42 (2H, br s, tetrahydropyridinyl CH$_2$), 2.69 (2H, t, J 7.9Hz, tetrahydropyridinyl CH$_2$), 3.18 (2H, br s, tetrahydropyridinyl CH$_2$), 3.78 (2H, ArCH$_2$N), 6.58 (1H, br s, tetrahydropyridinyl 5-H), 7.01–7.07 (1H, m, ArH), 7.16 (1H, s, ArH), 7.41 (1H, d, J 3.1Hz, ArH), 7.52–7.58 (1H, m, ArH), 8.05 (1H, d, J 11.3 Hz, ArH), 8.19–8.26 (2H, m, ArH), 8.68–8.72 (1H, m, ArH), 9.06 (1H, d, J 2.6 Hz, ArH), 11.51 (1H, br s, NH); m/z (ES$^+$) 358 (M+1)$^+$.

EXAMPLE 3

3-[4-(3-(4-Chlorophenyl)isoxazol-5-yl)-1,2,3,6-tetrahydropyridin-1-yl]methylpyrrolo[2,3-b]pyridine M.p. 245°–247° C. (toluene); (found: C, 67.52; H, 4.82; N, 14.19; C$_{22}$H$_{19}$N$_4$ClO requires C, 67.60; H, 4.90; N, 14.33%); δH (DMSO-d$_6$) 2.47 (2H, br s, tetrahydropyridinyl CH$_2$), 2.69 (2H, t, J 5.5 Hz, tetrahydropyridinyl CH$_2$), 3.18 (2H, br s, tetrahydropyridinyl CH$_2$), 3.79 (2H, ArCH$_2$N), 6.57 (1H, br s, tetrahydropyridinyl 5-H), 7.03–7.07 (2H, m, isoxazolyl 5-H), 7.41 (1H, br s, 2-H), 7.59 (2H, d, J 8.5 Hz, ArH), 7.89 (2H, d, J 8.5 Hz, ArH), 8.05 (1H, d, J 6.6 Hz, 4-H), 8.21 (1H, d, J 4.7 Hz, 6-H), 11.50 (1H, br s, NH); m/z (ES$^+$) 391 (M+1)$^+$.

EXAMPLE 4

3-[4-(1-Phenyl-1,2,3-triazol-4-yl)-1,2,3,6-tetrahydropyridin-1-yl]methylpyrrolo[2,3-]pyridine

Step 1: Phenylazide

Phenylhydrazine (6.7 g, 62 mmol) was added dropwise to a cold (0° C.) solution of concentrated hydrochloric acid (60 ml) over a period of 10 minutes. Diethyl ether (20 ml) was then added, followed by the dropwise addition of a solution of sodium nitrite (5 g, 72 mmol) in water (6 ml), keeping the temperature below 5° C. The reaction was then stirred at 0° C. for 1 hour and then extracted with ethyl acetate (3×100 ml). The combined organic layers were washed with water (2×50 ml), saturated brine (50 ml), dried (MgSO$_4$) and carefully evaporated in vacuo to give the crude title compound as a red oil (3.3 g, 45%).

Step 2: 1-tert-Butoxycarbonyl-4-(1-phenyl-1,2,3-triazol-4-yl)-tetrahydropyridine and 1-tert-butoxycarbonyl-4-(1-phenyl-1,2,3-triazol-5-yl)-1,2,3,6-tetrahydropyridine A mixture of the crude phenylazide (1.37 g, 11.5 mmol) from above and 1-tert-butoxycarbonyl-4-ethynyl-1,2,3,6-tetrahydropyridine (2 g, 9.6 mmol) (Example 1) in toluene (20 ml) was refluxed for 24 hours. The reaction was cooled and the solvent evaporated in vacuo. The crude residue was chromatographed on silica eluting with ethyl acetate/petrol (60°–80° C.) (1:2) to give the 1-tert-butoxycarbonyl-4-(1-phenyl-1,2,3-triazol-4-yl)-1,2,3,6-tetrahydropyridine as a tan waxy solid (853 mg, 27%), δH (CDCl$_3$) 1.49 (9H, s, OC(CH$_3$)$_3$), 2.59 (2H, br s, tetrahydropyridinyl CH$_2$), 3.67 (2H, t, J 5.2 Hz, tetrahydropyridinyl CH$_2$), 4.12 (2H, br s, tetrahydropyridinyl CH2), 6.53 (1H, br s, tetrahydropyridinyl 5-H), 7.42–7.46 (1H, m, ArH), 7.51–7.55 (2H, m, ArH), 7.72–7.75 (2H, m, ArH), 7.87 (1H, s, triazolyl 5-H).

Further elution yielded 1-tert-butoxycarbonyl-4-(1-phenyl-1,2,3-triazol-5-yl)-1,2,3,6-tetrahydropyridine as a buff solid (954 mg, 30%), δH (CDCl$_3$) 1.44 (9H, s, OC(CH$_3$)$_3$), 2.14 (2H, br s, tetrahydropyridinyl CH$_2$), 5.86 (1H, br s, tetrahydropyridinyl 5-H), 7.46–7.55 (5H, m, PhH), 7.67 (1H, s, triazolyl 4-H).

Step 3: 4-(1-Phenyl-1,2,3-triazol-4-yl)-1,2,3,6-tetrahydropyridine

To a solution of 1-tert-butoxycarbonyl-4-(1-phenyl-1,2,3-triazol-4-yl)-1,2,3,6-tetrahydropyridine (816 mg, 2.5 mmol) in dichloromethane (10 ml) was added trifluoroacetic acid (10 ml) and the reaction stirred at room temperature for 35 minutes. The solvent was evaporated in vacuo and the residue basfied by addition of aqueous sodium hydroxide (1M, 30 ml). Water (30 ml) was added and the mixture extracted with dichloromethane (3×30 ml). The combined organic layers were washed with saturated brine (20 ml), dried (K$_2$CO$_3$) and evaporated in vacuo to yield the title compound as a buff solid (486 mg, 86%). δH (CDCl$_3$) 2.59–2.53 (2H, br s, tetrahydropyridinyl CH$_2$), 3.14 (2H, t, J 5.7 Hz, tetrahydropyridinyl CH$_2$), 3.56–3.58 (2H, br s, tetrahydropyridinyl CH$_2$), 6.60 (1H, br s, tetrahydropyridinyl 5-H), 7.40–7.45 (1H, m, ArH), 7.50–7.54 (2H, m, ArH), 7.72–7.75 (2H, m, ArH), 7.84 (1H, s, triazolyl 5-H).

Step 4: 3-[4-(1-Phenyl-1,2,3-triazol-4-yl)-1,2,3,6-tetrahydropyridin-1-yl]methylpyrrolo[2,3-b]pyridine A mixture of the foregoing tetrahydropyridine (486 mg, 2.2 mmol) and 3-dimethylaminomethylpyrrolo[2,3-b]pyridine (438 mg, 2.5 mmol) in toluene (20 ml) was stirred at reflux for 16 hours. The reaction was cooled to room temperature and the precipitate collected by filtration, washed with toluene and dried. Recrystallisation from methanol gave the title compound as a buff solid (447 mg, 50%), m.p. 234°–236° C. (MeOH); (found: C, 70.70; H, 5.54; N, 23.19; C$_{21}$H$_{20}$N$_6$ requires C, 70.77; H, 5.66; N, 23.58%); δH (DMSO-d$_6$) 2.49 (2H, br s, tetrahydropyridinyl CH$_2$), 2.69 (2H, t, J 5.6 Hz, tetrahydropyridinyl CH$_2$), 3.13 (2H, br s, tetrahydropyridinyl CH$_2$), 3.77 (2H, s, ArH$_2$N), 6.45 (1H, br s, tetrahydropyridinyl 5-H), 7.02–7.05 (1H, m, 5-H), 7.40 (1H, br s, 2-H), 7.47 (1H, t, J 7.7 Hz, ArH), 7.59 (2H, t, J 7.6 Hz, ArH), 7.89 (2H, d, J 7.6 Hz, ArH), 8.06 (1H, d, J 7.8 Hz, 4-H), 8.20 (1H, d, J 4.8 Hz, 6-H), 11.48 (1H, br s, NH); m/z (ES$^+$), 357 (M+1)$^+$.

EXAMPLE 5

3-[4-(3-Biphenyl)-1,2,3,6-tetrahydropyridin-1-yl]methylpyrrolo[2,3-b]pyridine

Step 1: 1-tert-Butoxycarbonyl-4-hydroxy-4-(3-biphenyl) piperidine

To a solution of 3-bromobiphenyl (2.5 ml, 15 mmol) in tetrahydrofuran (50 ml) at −70° C. under a nitrogen atmosphere was added tert-butyllithium (1.7M in pentune, 9.7 ml, 16.5 mmol) keeping the temperature below −60° C. The reaction was stirred at −70° C. for 2 hours. A cold (−70° C.) solution of 1-tert-butoxycarbonyl-4-piperidone (2.7 g, 13.6 mmol) in tetrahydrofuran (50 ml) was then added keeping the temperature below −65° C. When addition was complete, the reaction was stirred at −70° C. for 30 mins and then allowed to warm to room temperature. After 1 hour at room temperature the reaction was cooled to 0° C. and quenched by addition of saturated aqueous ammonium chloride (10 ml). The mixture was warmed to room temperature, poured into water (500 ml) and extracted with ethyl acetate (2×250 ml). The combined extracts were washed with saturated brine (50 ml), dried (MgSO$_4$) and evaporated in vacuo to give the title compound as a light brown gum (4.9 g, 100%), which was used without further purification.

Step 2: 1-tert-Butoxycarbonyl-4-(3-biphenyl)-1,2,3,6-tetrahydropyridine

To a solution of the foregoing piperidinol (4.9 g, 13.6 mmol) in dichloromethane (10 ml) at −10° C. under nitrogen was added methanesulphonyl chloride (1.1 ml, 14 mmol) keeping the temperature below 0° C. The reaction was stirred at room temperature for 18 hours. The mixture was diluted with saturated aqueous sodium bicarbonate solution (50 ml), the phases separated and the aqueous phase extracted with dichloromethane (2×50 ml). The combined organic phases were washed with saturated brine (25 ml), dried (MgSO$_4$) and evaporated in vacuo to give a brown oil. This oil was dissolved in dichloromethane (10 ml), DBU (2.1 ml, 14 mmol) added and the reaction stirred at room temperature overnight. The resulting yellow solution was poured into citric acid (0.5M, 100 ml) and extracted with ethyl acetate (2×100 ml). The combined extracts were washed with saturated sodium bicarbonate solution (100 ml), saturated brine (100 ml), dried (MgSO$_4$) and evaporated in vacuo to give the title compound as a pale brown gum (1.47 g, 34%). δH (CDCl$_3$) 1.42 (9H, s, OC(CH$_3$)$_3$), 2.51 (2H, br s, tetrahydropyridinyl CH$_2$), 3.59 (2H, t, J 5 Hz, tetrahydropyridinyl CH$_2$), 4.03 (2H, br s, tetrahydropyridinyl CH$_2$), 6.02 (1H, br s, tetrahydropyridinyl 5-H), 7.27–7.42 (6H, m, ArH) 7.50–7.53 (3H, m, ArH).

Step 3: 4-(3-Biphenyl)-1,2,3,6-tetrahydropyridine

To a solution of the foregoing tetrahydropyridine (1.4 g, 4.2 mmol) in dichloromethane (10 ml) was added trifluoroacetic acid (10 ml) and the reaction stirred at room temperature for 15 minutes. The solvent was evaporated in vacuo and the residue partitioned between aqueous sodium hydroxide (1N, 50 ml) and dichloromethane (2×50 ml). The combined organics were washed with saturated brine (25 ml), dried (K$_2$CO$_3$) and evaporated in vacuo to give a brown gum. Purification by chromatography on silica eluting with dichloromethane/methanol/ammonia (90:8:1) afforded the title compound as a pale yellow oil (714 mg, 72%). δH (CDCl$_3$) 2.58 (2H, br s, tetrahydropyridinyl CH$_2$), 3.18 (2H, t, J 8.3 Hz, tetrahydropyridinyl CH$_2$), 3.29 (1H, br s, NH), 3.59–3.62 (2H, m, tetrahydropyridinyl CH$_2$), 6.16–6.19 (1H, m, tetrahydropyridinyl 5-H), 7.25–7.50 (6H, m, ArH), 7.57–7.61 (3H, m, ArH).

Step 4: 3-[4-(3-Biphenyl)-1,2,3,6-tetrahydropyridin-1-yl]methylpyrrolo[2,3-b]pyridine A mixture of the foregoing tetrahydropyridine (700 mg, 3 mmol) and 3-dimethylaminomethylpyrrolo[2,3-b]pyridine (495 mg, 2.8 mmol) in toluene (20 ml) was stirred at reflux for 15 hours. The reaction was cooled and the solvent evaporated in vacuo. Trituration of the residue with methanol gave an off-white solid. Recrystallization from propan-2-ol gave the title compound as a white solid (653 mg, 63%), m.p. 177°–178° C.; (found: C, 82.21; H, 6.27; N, 11.39; C$_{25}$H$_{23}$N$_3$ requires C, 82.16; H, 6.34; N, 11.50%); δH (DMSO-d$_6$) 2.51 (2H, br s, tetrahydropyridinyl CH$_2$), 2.68 (2H, t, J 8.2 Hz, tetrahydropyridinyl CH$_2$), 3.13 (2H, br s, tetrahydropyridinyl CH$_2$), 3.76 (2H, s, ArCH$_2$N), 6.24 (1H, br s, tetrahydropyridinyl 5-H), 7.02–7.06 (1H, m, Ar-H), 7.35–7.49 (7H, m, ArH), 7.65–7.69 (3H, m, ArH), 8.05 (1H, d, J 9.9 Hz, 4-H), 8.19 (1H, dd, J 6.6, 2.2 Hz, 6-H), 11.49 (1H, br s, NH); m/z (ES$^+$), 366 (M+1)$^+$.

EXAMPLE 6

3-[4-(4-Biphenyl)-1,2,3,6-tetrahydropyridin-1-yl] methylpyrrolo[2,3-b]pyridine hydrochloride M.p. >230° C. (dec.) (methanol); (found: C, 72.33; H, 6.12; N, 10.07; $C_{25}H_{23}N_3$, HCl 0.75 $H_2O$ requires C, 72.28; H, 6.19; N, 10.11%); δH ($CD_3OD$) 2.82 (1H, m, tetrahydropyridinyl H), 2.91 (1Hm, tetrahydropyridinyl H), 3.23 (1H, m, tetrahydropyridinyl H), 3.66 (1H, m, tetrahydropyridinyl H), 3.84 (2H, br s, tetrahydropyridinyl H's), 4.58 (2H, s, $ArCH_2N$), 6.24 (1H, br s, tetrahydropyridinyl 5-H), 7.19 (1H, dd, J 7.9, 4.6 Hz, 5-H), 7.20 (1H, t, J 7.3 Hz, ArH), 7.46–7.48 (2H, m, ArH), 7.55 (2H, d, J 8.5 Hz, ArH), 7.67–7.69 (4H, m, ArH), 7.85 (1H, d, J 2.5 Hz, 2-H), 8.30 (1H, dd, J 4.6, 1.4 Hz, 4-H), 8.34 (1H, m, 6-H), 11.00 (1H, br s, NH); m/z ($ES^+$), 366 $(M+1)^+$.

EXAMPLE 7

3-[4-(3-Phenyl-1,2,4-oxadiazol-5-yl)-1,2,3,6-tetrahydropyfidin-1-yl]methylpyrrolo[2,3-b]pyridine Step 1: Benzamide oxime To a stirred solution of sodium (0.48 g, 210 mmol) in methanol (210 ml) was added a solution of hydroxylamine hydrochloride (15.4 g, 221 mmol) in methanol (70 ml). The mixture was stirred at room temperature for 10 minutes before addition of benzonitrile (20.4 ml, 200 mmol) and the reaction stirred at room temperature overnight. The mixture was filtered through a pad of Celite and the flitrate concentrated in vacuo to approximately 100 ml. Diethyl ether (200 ml) was added and the precipitate filtered. The filtrate was evaporated in vacuo to dryness, and on drying the title compound was obtained as a waxy white solid (27.1 g, 100%). δH (DMSO-$d_6$) 5.92 (2H, br s, $NH_2$), 7.35–7.41 (3H, m, ArH), 7.65–7.91 (2H, m, ArH), 9.69 (1H, br s, OH).

Step 2: 3-Phenyl-5-(4-pyridyl)-1,2,4-oxadiazole

To a mixture of benzamide oxime (12.8 g, 94 mmol) and 4 Å sieves (80 g) in tetrahydrofuran (250 ml) under a nitrogen atmosphere was carefully added sodium hydride (55% dispersed in oil, 4.3 g, 98 mmol) portionwise. When addition was complete the reaction was heated at 50° C. for 1 hour. Methyl isonicotinamide (5.6 ml, 47 mmol) in tetrahydrofuran (50 ml) was added, and the reaction stirred at reflux for 2 hours. The reaction was cooled to room temperature and water (200 ml) and dichloromethane (300 ml) added. The mixture was filtered through a pad of Celite and the two phases separated. The aqueous phase was extracted with a further portion of dichloromethane (250 ml). The combined organic phases were washed with saturated brine (200 ml), dried ($MgSO_4$) and evaporated in vacuo. The residue was triturated with ethyl acetate to yield the title compound as a white solid (2.64 g, 25%). δH ($CDCl_3$) 7.50–7.56 (3H, m, ArH), 8.05–8.07 (2H, m, ArH), 8.16–8.19 (2H, m, ArH), 8.89 (2H, dd, J 4.4, 1.6 Hz, pyridyl 2-H, 6-H).

Step 3: 1-Benzyl-4-(3-phenyl-1,2,4-oxadiazol-5-yl)-1,2,3,6-tetrahydropyridine

To a suspension of the foregoing pyridine (2.6 g, 11.6 mmol) in DMF (5 ml) under a nitrogen atmosphere was added benzyl bromide (1.6 ml, 13.4 mmol) and the reaction heated at 100° C. for 1 hour. The reaction was cooled to room temperature and the mixture diluted with ethanol (4 ml). The solid was filtered, washed with ethanol (2×2 ml), and suspended in ethanol (45 ml). Sodium borohydride (574 mg, 15.1 mmol) was added portionwise and on completion of addition the reaction was stirred at room temperature for 2 hours. The solvent was evaporated in vacuo and the residue partitioned between water (40 ml) and ethyl acetate (2×40 ml). The combined organics were washed with saturated brine (40 ml), dried ($MgSO_4$) and evaporated in vacuo to a tan solid. Purification by chromatography on silica eluting with methanol/dichloromethane (1:4) gave the title compound as a white solid (1.22 g, 33%). δH ($CDCl_3$) 2.71–2.76 (4H, m, 2x tetrahydropyridinyl $CH_2$), 3.29 (2H, br s, tetrahydropyridinyl $CH_2$), 3.67 (2H, s, $PhCH_2N$), 7.05 (1H, br s, tetrahydropyridinyl 5-CH, 7.25–7.38 (5H, m, Ar-H), 7.45–7.50 (3H, m, ArH), 8.07–8.10 (2H, m, ArH).

Step 4: 4-(3-Phenyl1,2,4-oxadiazol-5-yl)-1,2,3,6-tetrahydropyridine hydrochloride To a solution of the tetrahydropyridine from the previous step (1.12 g, 3.5 mmol) in dichloromethane (15 ml) at 0° C. under a nitrogen atmosphere was added 1-chloroethyl chloroformate (0.5 ml, 4.3 mmol), keeping the temperature at 0° C. The mixture was stirred at 0° C. for 30 minutes and then at room temperature for 30 minutes. The solvent was evaporated and methanol (15 ml) was added to the residue. The mixture was heated at reflux for 20 minutes, and then cooled to room temperature. On cooling a precipitate formed which was collected by filtration, washed with methanol and dried to afford the title compound (390 mg, 42%). δH (DMSO-$d_6$) 2.83 (2H, br s, tetrahydropyridinyl $CH_2$), 3.35 (2H, t, J 6.0 Hz, tetrahydropyridinyl $CH_2$), 3.92 (2H, br s, tetrahydropyridinyl $CH_2$), 7.11 (1H, br s, tetrahydropyridinyl 5-H), 7.57–7.62 (3H, m, ArH), 8.02–8.05 (2H, m, ArH), 9.31 (1H, br s, NH).

Step 5: 3-[4-(3-Phenyl-1,2,4-oxadiazol-5-yl)-1,2,3,6-tetrahydropyridin-1-yl]methylpyrrolo[2,3-b]pyridine A mixture of the foregoing tetrahydropyridine free base (298 mg, 1.3 mmol) and 3-dimethylaminomethylpyrrolo[2,3-b]pyridine (218 mg, 1.2 mmol) in toluene (20 ml) was stirred at reflux overnight. On cooling a precipitate formed which was collected by filtration, washed with toluene and dried. Recrystallisation from methanol gave the title compound (184 mg, 41%), m.p. 207°–209° C.; (found: C, 70.38; H, 5.23; N, 19.42; $C_{21}H_{19}N_5O$ requires C, 70.57; H, 5.36; N, 19.59%); δH (DMSO-$d_6$) 2.60 (2H, br s, tetrahydropyridinyl $CH_2$), 2.71 (2H, t, J 5.2 Hz, tetrahydropyridinyl $CH_2$), 3.25 (2H, br s, tetrahydropyridinyl $CH_2$), 3.81 (2H, s, $ArCH_2N$, 7.03–7.07 (1H, m, ArH), 7.10 (1H, br s, tetrahydropyridinyl 5-H), 7.42 (1H, br s, ArH), 7.54–7.60 (3H, m, ArH), 8.00–8.06 (3H, m, ArH), 8.21 (1H, d, J 4.1 Hz, 6-H), 11.51 (1H, br s, NH); m/z ($ES^+$), 358 $(M+1)^+$.

EXAMPLE 8

3-[4-(5-Phenyloxazol-2-yl)-1,2,3,6-tetrahydropyridin-1-yl]methylpyrrolo[2,3-b]pyridine M.p. 212°–214° C. (dec.) (methanol); (found: C, 73.95; H, 5.42; N, 15.55; $C_{22}H_{20}N_4O$ requires C, 74.14; H, 5.66; N, 15.72%); δH (DMSO-$d_6$) 2.50 (2H, br s, tetrahydropyridinyl $CH_2$), 2.67 (2H, t, J 5.7 Hz, tetrahydropyridinyl $CH_2$), 3.19 (2H, br s, tetrahydropyridinyl $CH_2$), 3.79 (2H, s, $ArCH_2N$), 6.77 (1H, br s, tetrahydropyridinyl 5-H), 7.03–7.06 (1H), m, 5-H), 7.33–7.48 (4H, m, Ar-H), 7.67–7.74 (3H, m, ArH), oxazolyl 4-H), 8.05 (1H, d, J 7.4 Hz, 4-H), 8.21 (1H, d, J 4.3 Hz, 6-H), 11.49 (1H, br s, NH); m/z ($ES^+$), 357 $(M+1)^+$.

EXAMPLE 9

3-[4-(5-Phenylthien-2-yl)-1,2,3,6-tetrahydropyridin-1-yl] methylpyrrolo[2,3-b]pyridine Step 1: 2-Phenylthiophene To a solution of 2-iodothiophene (2.8 ml, 25 mmol) and palladium tetrakistriphenylphosphine (866 mg, 0.75 mmol) in toluene (50 ml) under a nitrogen atmosphere was added aqueous sodium carbonate (2M, 25 ml) followed by a solution of phenylboronic acid (3.7 mg, 30 mmol) in methanol (12.5 ml). The vigorously stirred mixture was heated at 80° C. for 6 hours and then cooled to room temperature. Aqueous sodium carbonate (2M, 125 ml), dichloromethane (250 ml) and 0.88 ammonia solution (12 ml) were added to the reaction. The two phases were separated, and the aqueous phase extracted with dichloromethane (50 ml). The combined organic phases were washed with brine (80 ml), dried (MgSO$_4$) and evaporated in vacuo to an oil. Purification by chromatography on silica gel eluting with hexane gave the title compound as a colourless oil (1.35 g, 36%) which solidified on standing. δH (CDCl$_3$) 7.06–7.09 (1H, m, ArH), 7.25–7.31 (3H, m, ArH), 7.35–7.39 (2H, m, ArH, 7.60–7.62 (2H, m, ArH).

Step 2: 1-tert-Butoxycarbonyl-4-hydroxy-4-(2-phenylthien-5-yl)piperidine

To a solution of 2-phenylthiophene (1.35 g, 9.1 mmol) in tetrahydrofuran (40 ml) at –40° C. under a nitrogen atmosphere was added a solution of n-butyllithium (1.6M in hexanes, 6 ml, 95 mmol) keeping the temperature below –40° C. The reaction was stirred at –40° C. for 10 minutes, allowed to warm to 0° C. and stirred at 0° C. for 30 minutes. The reaction was cooled to –78° C. and a solution of 1-tert-butoxycarbonyl-4-piperidone (1.8 g, 9.1 mmol) in tetrahydrofuran (20 ml) added, keeping the temperature below –50° C. When addition was complete, the reaction was stirred at –60° C. for 30 minutes and at room temperature for 1 hour. The reaction was cooled to 0° C. and quenched by addition of saturated aqueous ammonium chloride (10 ml), poured into water (100 ml) and extracted with ethyl acetate (3×50 ml). The combined extracts were washed with brine (50 ml), dried (MgSO$_4$) and evaporated in vacuo to an oil. Purification by chromatography on silica eluting with ethyl acetate/hexane (1:2) gave the title compound as a foam, (2.5 g, 76%). δH (CDCl$_3$) 1.41 (9H, s, OC(CH$_3$)$_3$), 1.84–1.97 (2H, m, piperidinyl H), 2.36 (1H, t, J 9.0 Hz, piperidinyl H), 3.20–3.28 (2H, m, piperidinyl H), 3.64 (1H, t, J 8.9 Hz, piperidinyl H), 3.82 (2H, m, piperidinyl H), 6.86–6.91 (1H, m, ArH), 7.09 (1H, m, ArH), 7.09 (1H, d, J 5.3 Hz, ArH), 7.16–7.33 (3H, m, ArH), 7.46–7.51 (2H, m, ArH).

Step 3: 4-(2-Phenylthien-5-yl)-1,2,3,6-tetrahydropyridine

To a solution of the foregoing piperidinol (2.4 g, 6.7 mmol) in dichloromethane (30 ml) was added trifluoroacetic acid (11 ml) and the reaction stirred at room temperature for 90 minutes. The solution was evaporated in vaccuo and the residue treated with aqueous sodium hydroxide (2M, 30 ml). The aqueous mixture was extracted with dichloromethane (3×50 ml). The combined organics were washed with saturated brine (40 ml), dried (K$_2$CO$_3$) and evaporated in vacuo to give the title compound as a beige solid (1.47 g, 91%). δH (CDCl$_3$) 2.39–2.48 (2H, m, tetrahydropyridinyl CH$_2$), 3.10 (2H, t, J 5.7 Hz, tetrahydropyridinyl CH$_2$), 3.51–3.53 (2H, m, tetrahydropyridinyl CH$_2$), 6.18 (1H, br s, tetrahydropyridinyl 5-H), 6.92–6.95 (1H, m, ArH), 7.17–7.18 (1H, m, ArH), 7.23–7.27 (1H, m, ArH), 7.33–7.38 (2H, m, ArH), 7.56–7.59 (2H, m, ArH).

Step 4: 3-[4-(5-Phenylthien-2-yl)-1,2,3,6-tetrahydropyridin-1-yl]methylpyrrolo[2,3-]pyridine A mixture of the foregoing tetrahydeopyridine (1.30 g, 5.4 mmol) and 3-dimethylaminomethylpyrrolo[2,3-b]pyridine (895 mg, 5.1 mmol) in toluene (25 ml) was heated at reflux for 22 hours. The reaction was cooled to room temperature, the precipitate filitered, washed with toluene and dried. Recrystallisation from toluene yielded the title compound (760 mg, 40%), m.p. 211°–213° C.; (found: C, 74.36; H, 5.64; N, 10.99; C$_{23}$H$_{21}$N$_3$S requires C, 74.36; H, 5.70; N, 11.31%); δH (DMSO-d$_6$) 2.47 (2H, br s, tetrahydropyridinyl CH$_2$), 2.67 (2H, t, J 5.7 Hz, tetrahydropyridinyl CH$_2$), 3.11 (2H, br s, tetrahydropyridinyl C$_2$), 3.76 (2H, s, ArCH$_2$N), 6.12 (1H, br s, tetrahydropyridinyl 5-H), 7.03–7.06 (2H, m, ArH), 7.24–7.31 (1H, m, ArH), 7.38–7.42 (4H, m, ArH), 7.62 (2H, d, J 7.3 Hz, ArH), 8.05 (1H, d, J 7.9 Hz, 4-H), 8.21 (1H, dd, J 4.7, 1.5 Hz, 6-H), 11.48 (1H, br s, NH); m/z (ES$^+$), 3.72 (MH)$^+$.

EXAMPLE 10 trans-3-[4-(2-Phenylcycloprop-1-yl)-1,2,3,6-tetrahydropdin-1-yl]methylpyrrolo[2,3-b]pyridine Step 1: trans-2-Phenyl-1-(4-pyridyl)cyclopropane To a mixture of (H)-4-(2-phenylethenyl)pyridine (1 g, 5.5 mmol) and trimethylsulphonium iodide (1.35 g, 6.62 mmol) in anhydrous DMSO (15 ml) was added potassium tert-butoxide (0.78 g)in DMSO (10 ml) dropwise, and the resultant red solution stirred at room temperature for 5 hours. At this stage a further portion of trimethylsulphonium iodide (1.35 g) was added to the reaction followed by dropwise addition of a solution of potassium tert-butoxide (0.78 g) in DMSO (12 ml). The reaction was stirred at room temperature for a further 48 hours. A final portion of trimethylsulphonium iodide (1.35 g) was added followed again by the dropwise addition of a solution of potassium tert-butoxide (0.78 g)in DMSO (10 ml). The reaction was stirred for a further 5 hours after which time it was diluted with water (500 ml) and stirred overnight. The mixture was extracted with ethyl acetate (2×200 ml) and the combined extracts washed with saturated brine (200 ml), dried (MgSO$_4$) and evaporated in vacuo to give an oil (0.93 g, 86%) which partially crystallised. NMR showed this to be a 5:1 inseparable mixture of product and starting material. δH (CDCl$_3$) 1.47–1.62 (2H, m, cyclopropyl CH$_2$), 2.07–2.14 (1H, m, cyclopropyl CH), 2.21–2.29 (1H, m, cyclopropyl CH), 7.11–7.39 (7H, m, ArH), 8.47 (2H, br s, pyridyl 2-H, 6-H).

Step 2: trans-1-Benzyl-4-(2-phenylcyclopropyl-1-yl)-1,2,3,6-tetrahydropyridine

The mixture from the preceding step (0.91 mg, 4.66 mmol) was dissolved in DMF (5 ml), benzyl bromide (0.61 ml, 5.1 mmol) added and the reaction stirred at 110° C. for 90 minutes. The mixture was cooled to room temperature, diluted with ethanol (50 ml) and sodium borohydride (0.22 g, 5.8 mmol) added in portions. The reaction was stirred at room temperature overnight. The mixture was concentrated in, vacuo, water (100 ml) added and extracted with ethyl acetate (2×100 ml). The combined organics were washed with saturated brine (100 ml), dried (MgSO$_4$) and evaporated. The residue was dissolved in 10% ethyl acetate/dichloromethane (50 ml) and treated with silica (10 g). The silica was removed by filtration, washed with 10% ethyl acetate/dichloromethane (2×50 ml) and the flitrate evaporated to an oil (0.99 g, 75%). NMR showed this to be a 4:1 mixture of required product to stilbazole derived product. δH (CDCl$_3$) 1.01–1.08 (1H, m, cyclopropyl H), 1.15–1.25 (1H, m, cyclopropyl H), 1.57–1.64 (1H, m, cyclopropyl H), 1.90–1.98 (1H, m, cyclopropyl H), 2.10 (2H, br s, tetrahydropyridinyl CH$_2$), 2.58 (2H, t, J 8.3 Hz, tetrahydropyridinyl CH$_2$), 2.99 (2H, br s, tetrahydropyridinyl CH$_2$), 3.59 (2H, s, PhCH$_2$N), 5.45 (1H, br s, tetrahydropyridinyl 5-H), 7.04–7.41 (10H, m, Ar-H).

Step 4: Trans-3-[4-(2-Phenylcycloprop-1-yl)-1,2,3,6-tetrahydropyridin-1-yl]methypyrrolo[2,3-b]pyridine To a solution of the foregoing oil (0.98 g, 3.4 mmol) in dichloromethane (15 ml) at 0° C. was added 1-chloroethyl chloroformate (0.47 ml, 4.36 mmol) keeping the temperature below 0° C. The reaction was stirred at 0° C. for 1 hour, after which the solvent was evaporated in vacuo. Methanol (20 ml) was added and the reaction stirred at reflux for 1.5 hours. The reaction was cooled, concentrated in vacuo and saturated aqueous potassium carbonate (50 ml) added. The mixture was extracted with dichloromethane (2×50 ml). The combined extracts were washed with saturated brine (50 ml), dried (MgSO$_4$) and evaporated to an oil. Toluene (15 ml) was added to the oil followed by 3-dimethylaminomethylpyrrolo[2,3-b]pyridine (0.59 g, 3.37 mmol) and the mixture heated at reflux for 7 hours. The reaction was cooled, the precipitate filtered, washed with toluene (10 ml) and the filtrate concentrated in vacuo. The residue was chromatographed on silica eluting with methanol/dichloromethane (5 to 10%) to give the title compound as a brown glass (90 mg, 8%). Further purification was achieved by formation of the oxalate salt which was recrystallised from propan-2-ol to afford the oxalate of the title compound (48.4 mg), m.p.>100° C. (collapses to a gum); (found: C, 66.76; H, 6.21; N, 9.17; C$_{22}$H$_{23}$N$_3$, C$_2$H$_2$O$_4$, 0.5H$_2$O, 0.5 (C$_3$H$_8$O) requires C, 66.80; H, 6.59; N, 9.16%); δH (DMSO-d$_6$) 1.09–1.11 (1H, m, cyclopropyl H), 1.23 (1H, m, cyclopropyl H), 1.68 (1H, m, cyclopropyl H), 2.01 (1H, m, cyclopropyl H), 2.23 (2H, br s, tetrahydropyridinyl CH$_2$), 3.21 (2H, br s, tetrahydropyridinyl CH$_2$), 3.55 (2H, br s, tetrahydropyrnyl CH$_2$), 4.39 (2H, s, ArCH$_2$N), 5.50 (1H, br s, tetrahydropyridinyl 5-H), 7.08–7.26 (6H, m, ArH), 7.66 (1H, s, ArH), 8.18 (1H, d, J 6.7 Hz, 4-H), 8.27 (1H, d, J 3.2 Hz, 6-H), 11.97 (1H, br s, NH); m/z (ES$^+$), 330 (M+1)$^+$.

What is claimed is:

1. A compound of formula I, or a salt thereof:

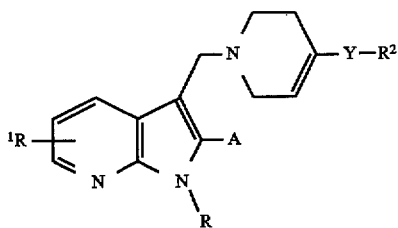

(I)

wherein

A represents hydrogen, C$_{1-6}$ alkyl, C$_{1-6}$ alkoxy, halogen, cyano or trifluoromethyl;

R$^1$ represents hydrogen, halogen, cyano, nitro, trifluoromethyl, amino, C$_{1-6}$ alkylamino, di(C$_{1-6}$) alkylamino, C$_{1-6}$ alkyl, C$_{1-6}$ alkoxy, aryl(C$_{1-6}$)alkoxy or C$_{2-6}$ alkylcarbonyl;

Y represents a divalent monocyclic radical selected from the following groups of formula Ya to Yg:

 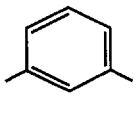 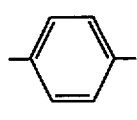 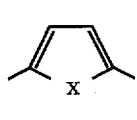
(Ya) (Yb) (Yc) (Yd)

-continued

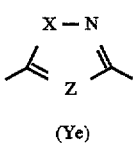 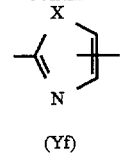 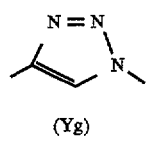
(Ye) (Yf) (Yg)

in which X represents oxygen, sulphur or N—R$^3$;

Z represents CH or N;

R and R$^3$ independently represent hydrogen or C$_{1-6}$alkyl; and

R$^2$ represents an optionally substituted aryl or heteroaryl group, wherein aryl is selected from the group consisting of phenyl and naphthyl and heteroaryl is selected from the group consisting of pyridyl, quinolyl, isoquinolyl, pyridazinyl, pyrirnidinyl, pyrazinyl, pyranyl, furyl, benzofuryl, dibenzofuryl, thienyl, benzthienyl, pyrrolyl, indolyl, pyrazolyl, indazolyl, imidazolyl, benzimidazolyl, oxazolyl, isoxazolyl, oxadiazolyl, thiazolyl, isothiazolyl and thiadiazolyl, and the substituents are selected from the group consisting of C$_{1-6}$alkyl, adamantyl, phenyl, aryl(C$_{1-6}$)alkyl, halogen, C$_{1-6}$haloalkyl, C$_{1-6}$aminoalkyl, trifluoromethyl, hydroxy, C$_{1-6}$alkoxy, aryloxy, C$_{1-3}$alkylenedioxy, nitro, cyano, carboxy, C$_{2-6}$alkoxycarbonyl, C$_{2-6}$alkoxycarbonyl(C$_{1-6}$)alkyl, C$_{2-6}$alkylcarbonyloxy, arylcarbonyloxy, C$_{2-6}$alkylcarbonyl, arylcarbonyl, C$_{1-6}$alkylthio, C$_{1-6}$alkylsulphinyl, C$_{1-6}$alkylsulphonyl, arylsulphonyl, trifluoromethanesulphonyloxy, —NR$^v$R$^w$, —NR$^v$COR$^w$, —NR$^v$CO$_2$R$^w$, —NR$^v$SO$_2$R$^w$, —CH$_2$NR$^v$SO$_2$R$^w$, —NHCONR'R$^w$, PO(OR")(OR'''), —CONR'R$^w$, —SO$_2$NR'R$^w$ and —CH$_2$SO$_2$NR'R$^w$ in which R$^v$ and R$^w$ independently represent hydrogen, C$_{1-6}$alkyl, aryl or aryl(C$_{1-6}$)alkyl.

2. A compound as claimed in claim 1 wherein R$^2$ represents phenyl, fluorophenyl, chlorophenyl, methylphenyl, methoxyphenyl or pyridyl.

3. A compound as claimed in claim 1 represented by formula IIA, or salt thereof:

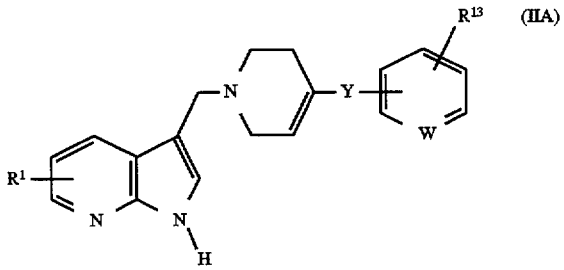

(IIA)

wherein

R$^1$ and Y are as defined in claim 1;

W represents CH or N; and

R$^{13}$ represents hydrogen, halogen, cyano, nitro, trifluoromethyl, C$_{1-6}$ alkyl, C$_{1-6}$ alkoxy or di(C$_{1-6}$) alkylamino.

4. A compound as claimed in claim 3 wherein R$^{13}$ represents hydrogen, fluoro, chloro, cyano, nitro, trifluoromethyl, methyl, methoxy or dimethylamino.

5. A compound selected from:

3-[4-(3-phenylisoxazol-5-yl)-1,2,3,6-tetrahydropyridin-1-yl]methylpyrrolo[2,3-b]pyridine;

3-[4-(3-(pyridin-3-yl)isoxazol-5-yl)-1,2,3,6-tetrahydropyridin-1-yl]methylpyrrolo[2,3-b]pyridine;

3-[4-(3-(4-chlorophenyl)isoxazol-5-yl)-1,2,3,6-tetrahydropyriden-1-yl]methylpyrrolo[2,3-b]pyridine;

3-[4-(1-phenyl-1,2,3-triazol-4-yl)-1,2,3,6-tetrahydropyridin-1-yl]methylpyrrolo[2,3-b]pyridine;

3-[4-(3-biphenyl)-1,2,3,6-tetrahydropyridin-1-yl]methylpyrrolo[2,3-b]pyridine;

3-[4-(4-biphenyl)-1,2,3,6-tetrahydropyridin-1-yl]methylpyrrolo[2,3-b]pyridine;

3-[4-(3-phenyl-1,2,4-oxadiazol-5-yl)-1,2,3,6-tetrahydropyridin-1-yl]methylpyrrolo[2,3-b]pyridine;

3-[4-(5-phenyloxazol-2-yl)-1,2,3,6-tetrahydropyridin-1-yl]methylpyrrolo[2,3-b]pyridine;

3-[4-(5-phenylthien-2-yl)-1,2,3,6-tetrahydropyridin-1-yl]methylpyrrolo[2,3-b]pyridine;

trans-3-[4-(2-phenylcyclopropyl-1-yl)-1,2,3,6-tetrahydropyridin- 1-yl]methylpyrrolo[2,3-b]pyridine;

or salt thereof.

6. A pharmaceutical composition comprising an effective amount of a compound of formula I as defined in claim 1, or a pharmaceutically acceptable salt thereof, in association with a pharmaceutically acceptable carrier.

7. A method for the treatment of schizophrenia and depression, which comprises administering to a patient in need of such treatment an effective amount of a compound of formula I as defined in claim 1, or a pharmaceutically acceptable salt thereof.

* * * * *